(12) United States Patent
Hinterlong

(10) Patent No.: US 8,081,083 B2
(45) Date of Patent: Dec. 20, 2011

(54) MATTRESS OR CHAIR SENSOR ENVELOPE WITH AN ANTENNA

(75) Inventor: Stephen Joseph Hinterlong, Elburn, IL (US)

(73) Assignee: Telehealth Sensors LLC, Batavia, IL (US)

( * ) Notice: Subject to any disclaimer, the term of this patent is extended or adjusted under 35 U.S.C. 154(b) by 323 days.

(21) Appl. No.: 12/399,921

(22) Filed: Mar. 6, 2009

(65) Prior Publication Data

US 2010/0225489 A1    Sep. 9, 2010

(51) Int. Cl.
   G08B 23/00    (2006.01)
(52) U.S. Cl. .................. 340/573.4; 340/573.1; 600/300
(58) Field of Classification Search .............. 340/573.4, 340/573.1, 573.5; 455/41.2; 600/300, 301
   See application file for complete search history.

(56) References Cited

U.S. PATENT DOCUMENTS

| | | | |
|---|---|---|---|
| 4,907,845 A * | 3/1990 | Wood .......................... 340/573.4 |
| 5,268,670 A | 12/1993 | Brasch | |
| 5,494,046 A | 2/1996 | Cross | |
| 6,067,019 A * | 5/2000 | Scott .......................... 340/573.4 |
| 6,166,644 A | 12/2000 | Stroda | |
| RE37,467 E | 12/2001 | Brasch | |
| 6,546,813 B2 | 4/2003 | Hubbard, Jr. | |
| 6,611,206 B2 | 8/2003 | Eshelman | |
| 6,840,117 B2 | 1/2005 | Hubbard, Jr. | |
| 6,917,293 B2 * | 7/2005 | Beggs ........................ 340/573.1 |
| 6,968,294 B2 | 11/2005 | Gutta | |
| 7,154,397 B2 | 12/2006 | Zerhusen | |
| 7,256,708 B2 | 8/2007 | Rosenfeld | |
| 7,319,386 B2 | 1/2008 | Collins, Jr. | |
| 7,378,975 B1 | 5/2008 | Smith | |
| 7,538,659 B2 * | 5/2009 | Ulrich et al. ............. 340/286.07 |
| 7,746,218 B2 * | 6/2010 | Collins et al. ............ 340/286.07 |
| 2001/0001237 A1 | 5/2001 | Stroda | |
| 2002/0067273 A1 | 6/2002 | Jaques | |
| 2002/0169583 A1 | 11/2002 | Gutta | |
| 2003/0058111 A1 | 3/2003 | Lee | |
| 2007/0210917 A1 | 9/2007 | Collins, Jr. | |
| 2007/0288263 A1 | 12/2007 | Rodgers | |
| 2008/0004904 A1 * | 1/2008 | Tran ......................... 340/539.11 |
| 2008/0021731 A1 | 1/2008 | Rodgers | |
| 2008/0077436 A1 | 3/2008 | Muradia | |
| 2008/0091470 A1 | 4/2008 | Muradia | |
| 2008/0097176 A1 | 4/2008 | Music | |
| 2008/0224861 A1 | 9/2008 | McNeely | |
| 2009/0289800 A1 * | 11/2009 | Hansen ..................... 340/573.1 |
| 2010/0057543 A1 * | 3/2010 | Dring et al. ............... 340/573.1 |

FOREIGN PATENT DOCUMENTS

EP    1818843 A2    8/2007
WO    WO2008135985 A1    11/2008

* cited by examiner

*Primary Examiner* — Eric M Blount

(57) ABSTRACT

A pressure-actuated floor mat, mattress or chair pressure sensor is enclosed within a flexible protective envelope that is provided with active electronic devices that can monitor the state of the sensor but which can also wirelessly transmit signals carrying information from the sensor-detecting electronics. Radio signals carrying information about the sensor are transduced or emitted from a small antenna within, or attached to the one of the envelopes surfaces. A receiver receives the signals emitted from the antenna and relays the information to a remote patient monitoring system is realized by the electronics and sensor within a disposable protective envelope.

22 Claims, 14 Drawing Sheets

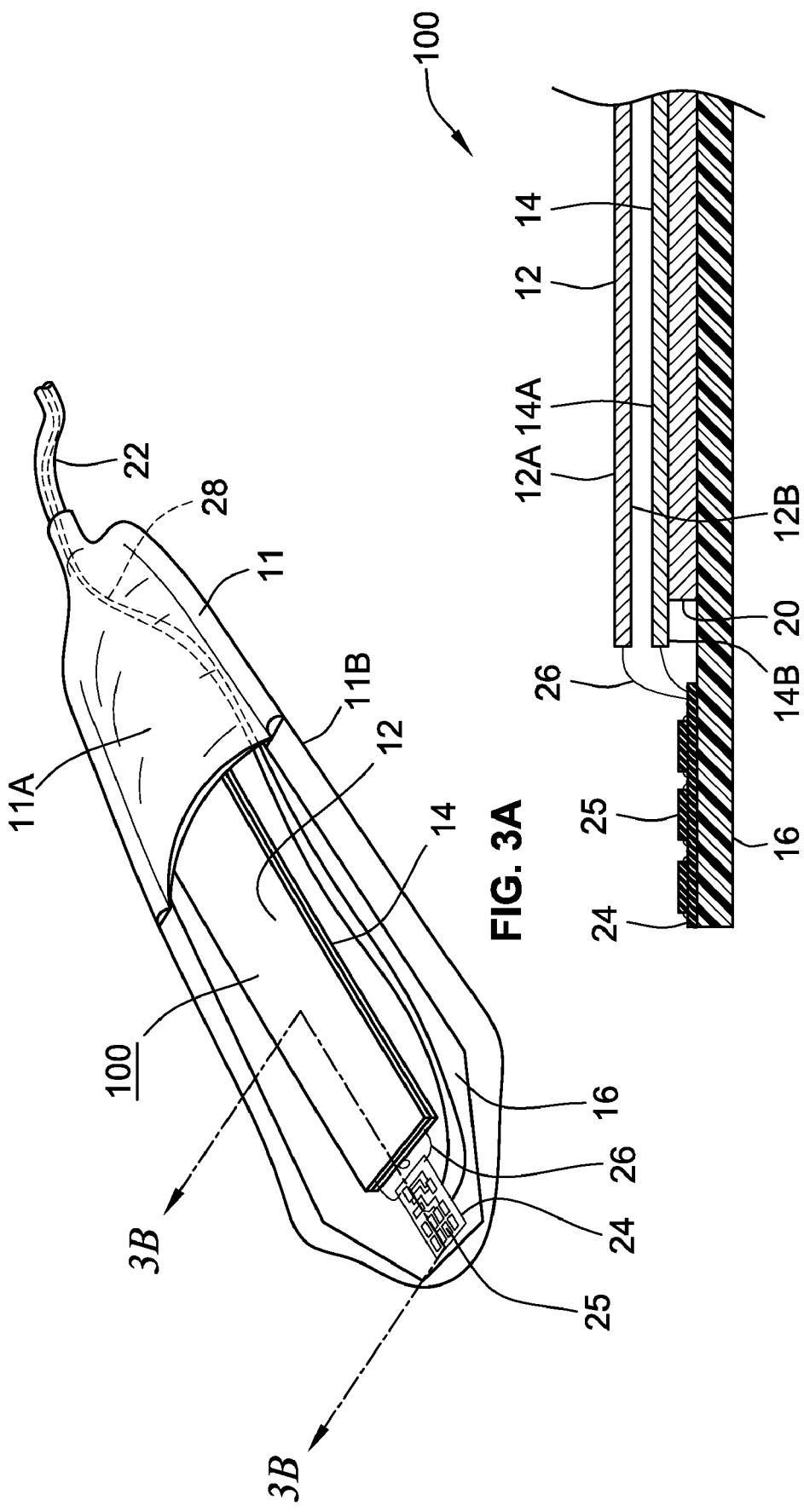

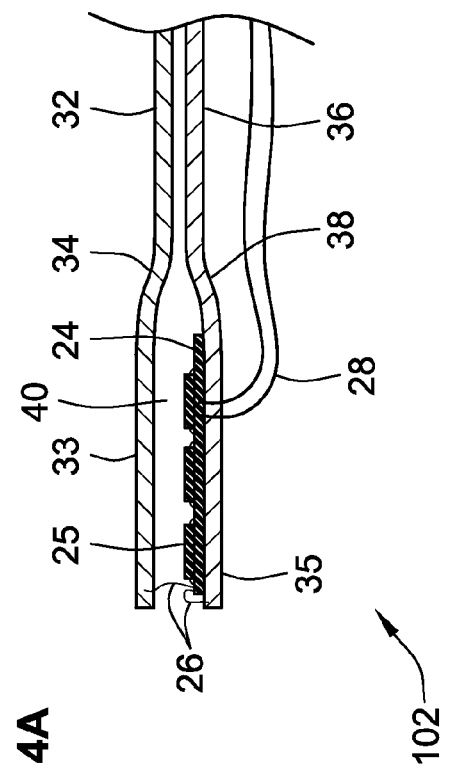
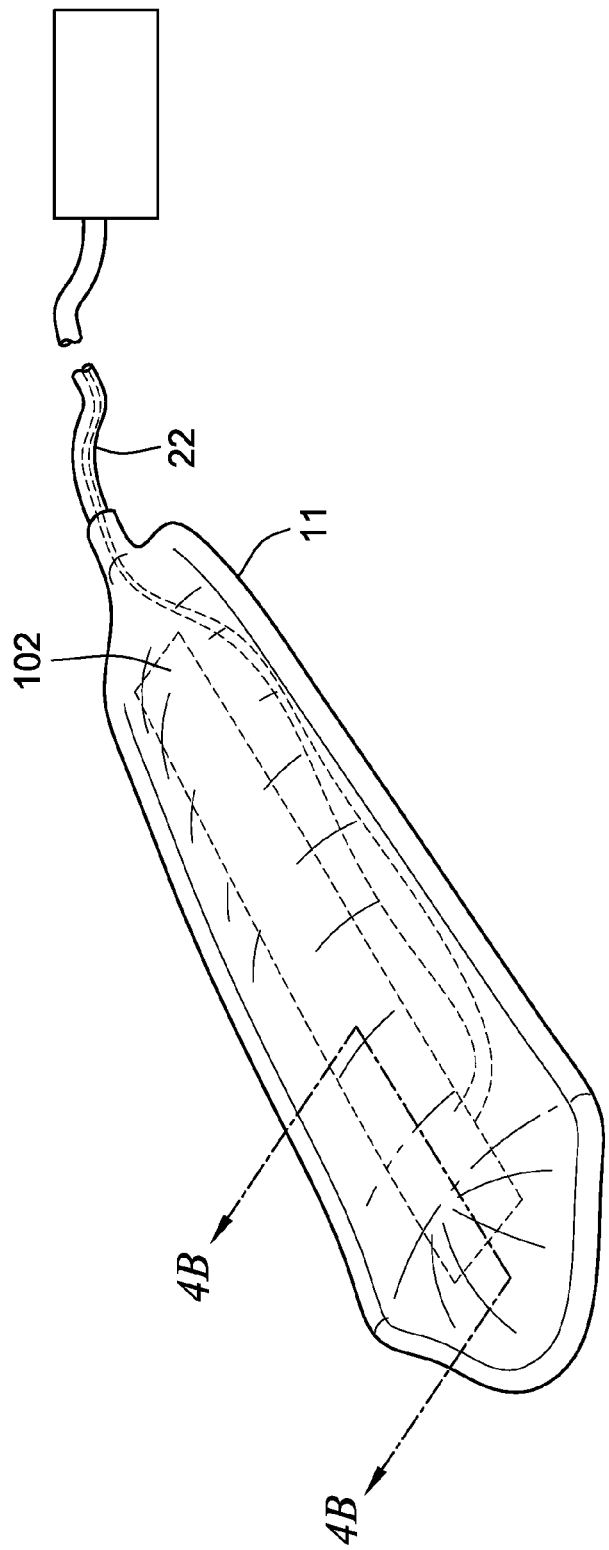
FIG. 4A
FIG. 4B

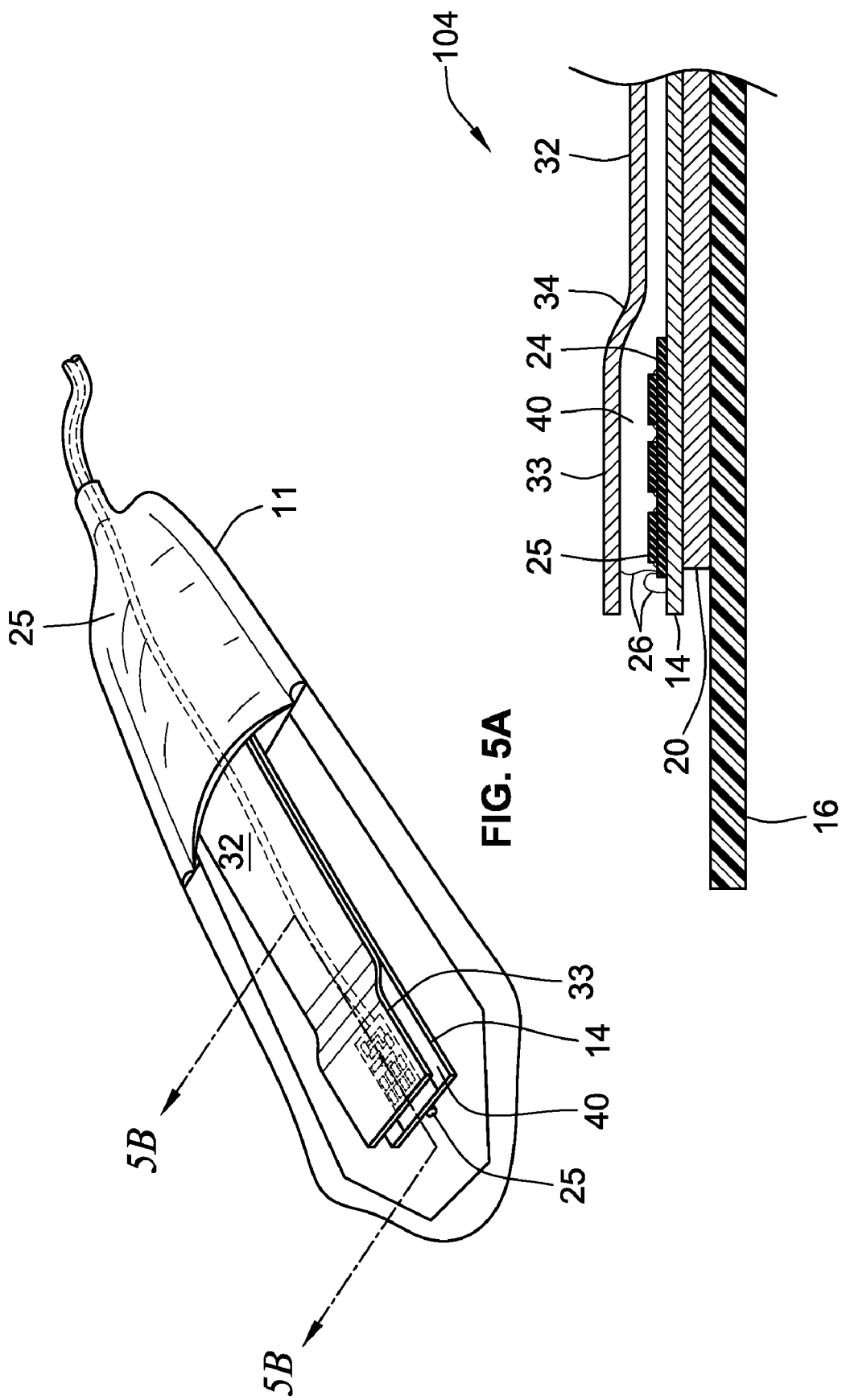

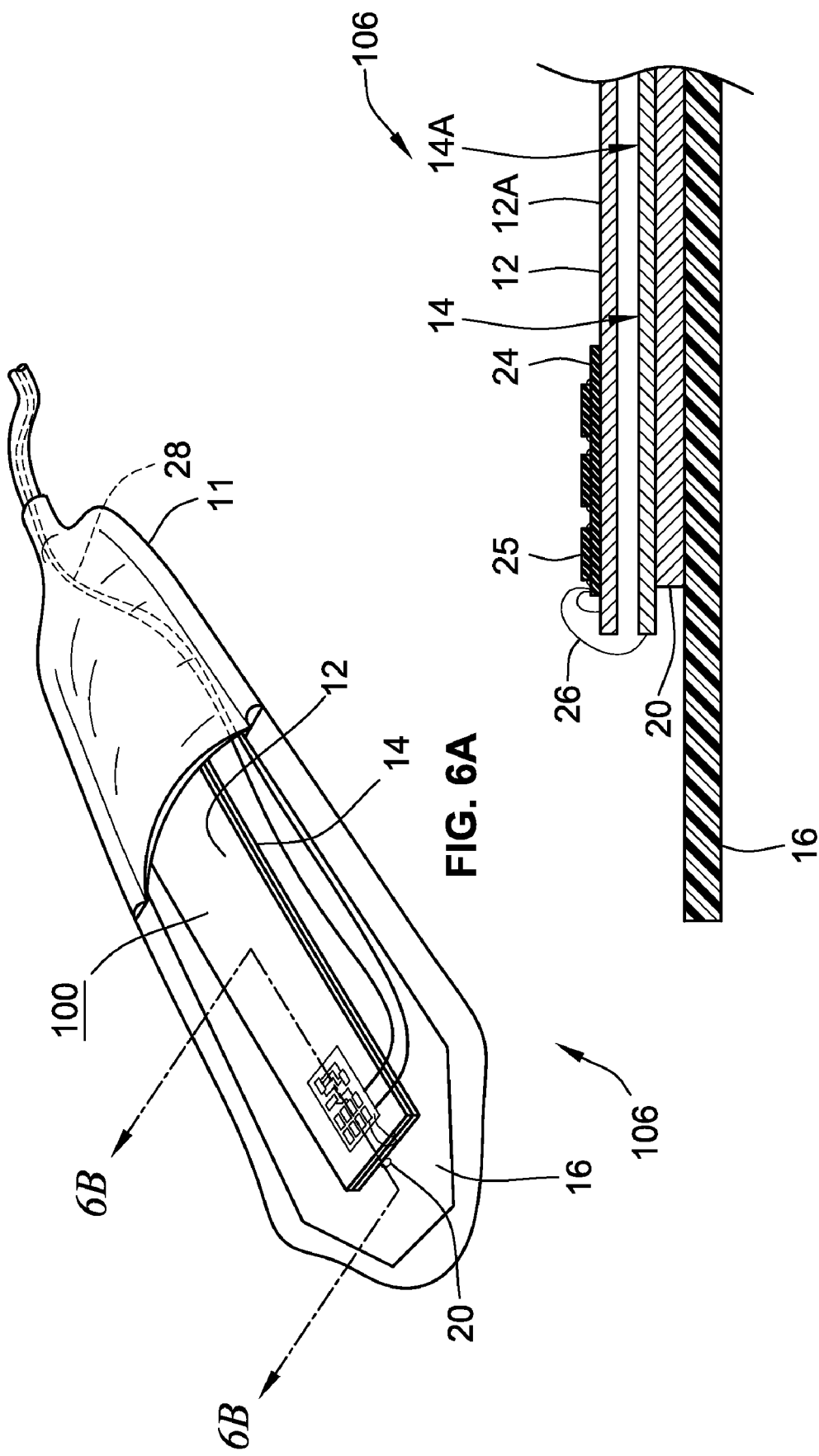

MATTRESS OR CHAIR SENSOR ENVELOPE WITH AN ANTENNA

BACKGROUND

FIG. 1 and FIG. 2 depict a prior art pressure sensor 10 mounted on a flexible plastic substrate 16. The sensor 10 and the substrate 16 are both enclosed within a protective flexible plastic sleeve 11. The sensor 10 is used to detect or sense a person lying in a bed or sitting in a chair. The sleeve 11 protects the sensor 10, especially from liquids.

The sensor 10 is comprised of two, thin, flat and elongated conductive panels 12 and 14. The panels 12 and 14 are kept spaced apart from each other by non-conductive spacers 13 and 15 applied to one or both of the sides of the panels 12 and 14 that face each other. Each of the panels 12 and 14 has a top side 12A and 14A and a bottom side, 12B and 14B. The spacers 13 and 15 are embodied as thin, narrow and elongated, adhesive-backed non-conductive strips that run along the side edges of a panel 12 and 14.

In FIG. 2, the top panel 12 is shown having two spacers that are identified by reference numeral 13 and which are attached to the lower face 12B of the top panel 12. The lower or bottom panel 14 is shown as having two spacers 15 that run along the side edges of the upper surface 14A of the bottom panel 14. Both sides of the spacers 13 and 15 have an adhesive backing, to affix the corresponding spacer to the surface of a panel.

The spacers 13 and/or 15 hold the panels 12 and 14 away from each other by a fixed distance that is equal to the spacer thickness. The spacers thus electrically isolate or separate the panels 12 and 14 from each other.

As can be seen in FIG. 2, an elongated fulcrum wire 20 is located between the second side 14B of the lower panel 14 and a relatively stiff, non-conductive switch-supporting substrate 16. The fulcrum wire 20 is centered or substantially centered between the two long, side edges of the lower panel 14 and runs almost the entire length of the lower panel 14.

When a force is applied to the top panel 12 either directly or through the envelope 11, the applied force will cause the panels 12 and 14 to bend around the fulcrum wire 20. Bending the panels 12 and 14 around the fulcrum wire 20 causes the outside edges of the panels to deflect downward toward the substrate 16, effectively causing the top surface 14A of the lower panel 14 to approach and eventually make contact with the bottom surface 12B of the upper panel 12. Bending the panels 12 and 14 around the fulcrum wire 20 thus eventually causes the bottom panel 14 to make a direct connection with the conductive top panel 12.

When the top panel 12 and the bottom panel 14 electrically contact each other in response to a pressure or force applied to the top panel, the structure shown in FIG. 2 functions as a switch. The switch/sensor 10 "closes" when a force sufficient to bend the panels 12 and 14 around the fulcrum wire 20 causes the two panels to make an electrical connection between them. The switch/sensor 10 opens when a switch-closing force is removed.

The amount of force required to close the switch/sensor 10 will depend on several different physical factors that include the width and thickness of each of the panels 12 and 14 as well as the material from which the panels 12 and 14 are fabricated. The thickness and width of the spacers 13 and/or 15 will also affect or determine the amount of pressure required to close the switch. Finally, the diameter and construction of the fulcrum wire 20 will also affect or determine the amount of pressure required to deform or bend the panels 12 and 14 such that they make electrical contact to each other. Experimentation has empirically determined the parameters of switches that will "close" at specific pressures.

It should be understood that as used herein, the term "sensor" refers to a two-state pressure-responsive switch which closes in response to an applied force, the required magnitude of which depends on one or more of the factors mentioned above. The terms "sensor" and "pressure sensor" should not be confused with a transducer, which is considered herein to be a device that generates, creates or outputs a signal representative of a measurable electrical characteristic of a sensor and/or the panels it is constructed from.

While the prior art sensors depicted in FIG. 1 and FIG. 2 have proven to be functionally adequate for detecting the presence or absence of a person on a mattress or sitting in a chair, they are somewhat deficient in their ability to work with patient monitoring systems that provide patient data to remotely located health care providers or patient monitors.

The prior art sensor 10 depicted in FIG. 1 and FIG. 2 tends to break down over time because of the environments in which they are typically used. Water, cleaning solutions and body fluids often leak into the sleeve 11, or the sleeve is punctured, the result of which is short-circuiting of the conductive panels 12 and 14. Electrical connections between the panels 12 and 14 and an external connector which runs through a cable 22 can also corrode. Providing some electronic intelligence to the sensor 10 that would enable the sensor 10 to be more reliable for use with remote or wireless patient monitoring systems and which might enable testing the sensor's functionality would be an improvement over the prior art.

BRIEF DESCRIPTION OF THE DRAWINGS

FIG. 3A is a perspective view of a cutaway of a pressure sensor that encloses an active electronic device mounted on a circuit board;

FIG. 3B is a cross-sectional view taken through section lines 3B-3D;

FIG. 4A is a perspective view of another embodiment of a pressure sensor such as the one show in FIG. 1 and FIG. 2 but having an electronic device mounted on a circuit board;

FIG. 4B is a cross-sectional view of the sensor shown in FIG. 4A taken through section lines 4B-4B;

FIG. 5A is another perspective view of a cutaway of a pressure sensor having an electronic device;

FIG. 5B is a cross-sectional view of a sensor shown in FIG. 5A through section lines 5B-5B;

FIG. 6A is a perspective view of a cutaway of another pressure sensor provided with an electronic device;

FIG. 6B is a cross-sectional view of the device shown in FIG. 6A taken through section lines 6B-6B;

DETAILED DESCRIPTION

Figure 1:
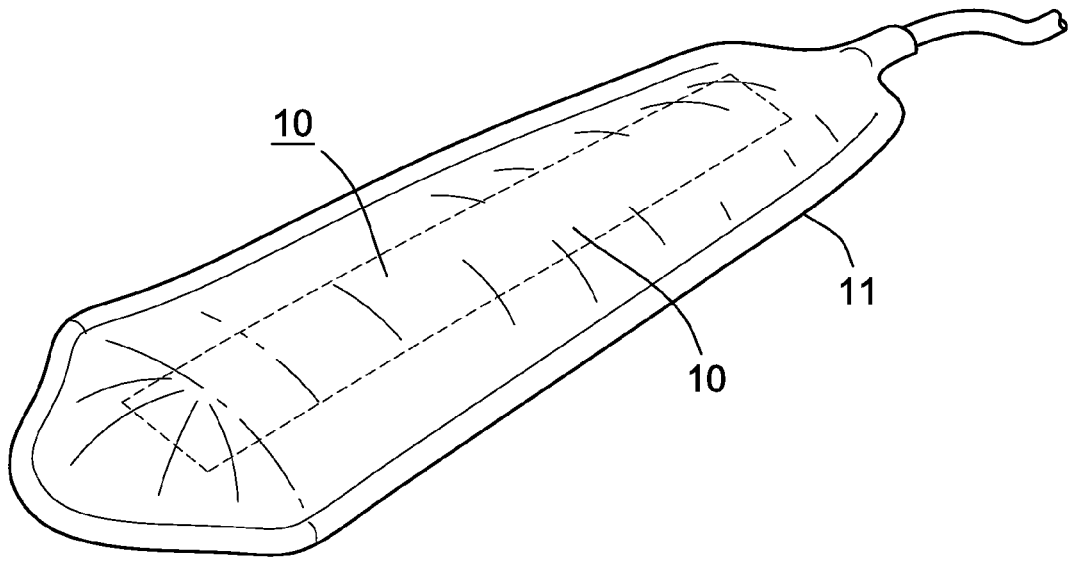
FIG. 1 is a perspective view of a prior art pressure sensor enclosed with a protective sleeve.
Figure 2:
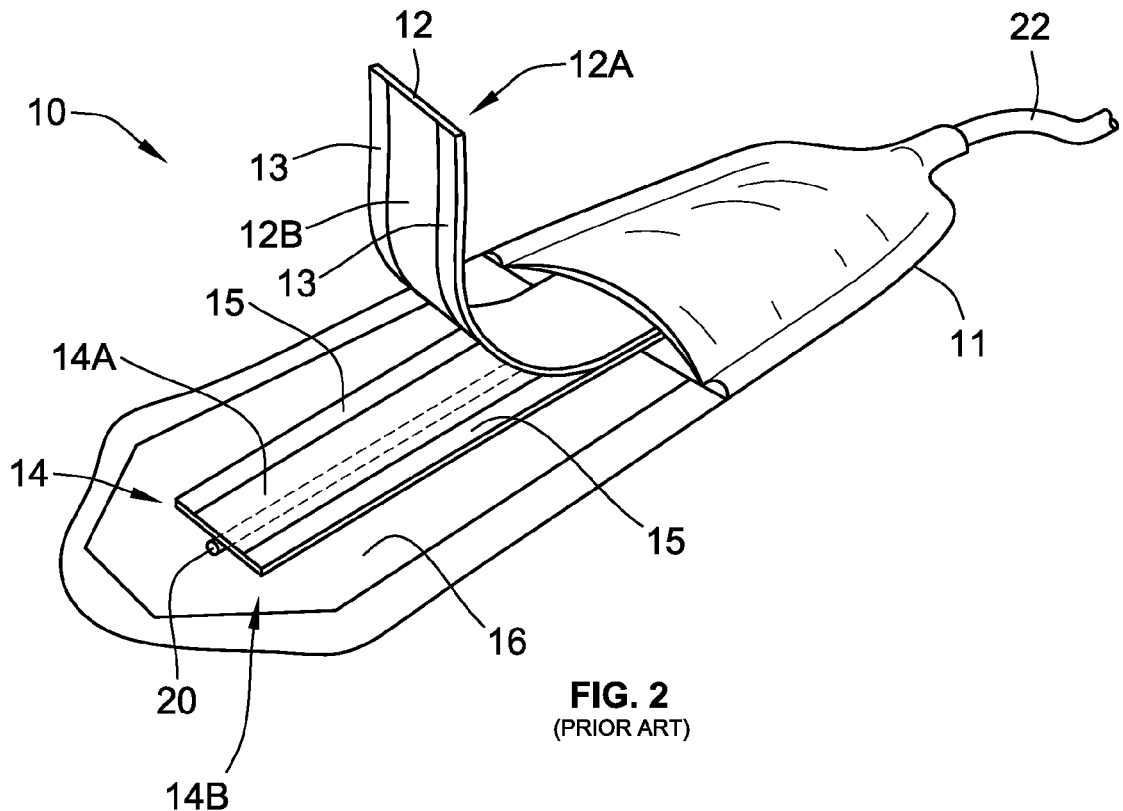
FIG. 2 is a partially-exploded view of the pressure sensor depicted in FIG. 1.

FIG. 3A is a perspective view of a first embodiment of a sensor 100 that acts as a switch and which has a circuit board 24 with one or more active electronic devices 25 that monitor the state of the sensor 100 when the sensor 100 is mounted and enclosed within a protective envelope or sleeve 11. The sensor 100 is comprised of a top panel 12, bottom panel 14 and fulcrum wire 20. The panels 12 and 14 are comprised of thin, elongated conductive strips that are preferably metal, separated from each other by the aforementioned spacers 13 and 15, but which are not shown in the figure for clarity. Their widths, thicknesses and constituent materials determine their flexural rigidity, which determines the force required to effectuate closure of the sensor 100, as happens when a force is applied orthogonal to the top surface 12A of the top panel 12, which is of a magnitude sufficient to bend the panels around the fulcrum wire 20.

FIGS. 3A and 3B show the panels 12 and 14 mounted to a substrate 16. The substrate 16 shown in the figures is rectangular except that its corners are either removed as shown or rounded in order to prevent or reduce the likelihood that a corner of the substrate pierces the envelope 11 that encloses the panels and substrate.

The substrate 16 is typically made from a non-conductive plastic such as high-density polyethylene (HDPE) or equivalents thereof. As shown in the figures, the substrate 16 provides a relatively large-area platform that can sit on a soft surface such as a mattress or chair cushion and thereby provide a relatively rigid surface for the fulcrum wire 20. The relatively large area of the substrate 16 prevents the substrate 16 from being driven downward into a mattress or chair pad due to the force applied to top surface of the top panel 12. In alternate embodiments, the substrate 16 can have other shapes, examples of which include square, round, elliptical and triangular, all of which are considered to be equivalents and within the scope of the term, substrate.

The envelope 11 forms a shell for the sensor 100 and the circuit board 24. The envelope 11 is comprised of a top half 11A and a bottom half 11B that are made from a relatively thin, flexible dielectric material that allows radio-frequency (RF) signals to pass through. High density polyethylene (HDPE) and low density polyethylene (LDPE) are examples of materials that can be used to form the envelope.

The sensor 100 is assembled by placing the top panel 12, the bottom panel 14, the circuit board 24, and the substrate and fulcrum wire 20 if provided, between the top 11A and bottom 11B halves of the envelope 11 and joining the two halves of the envelope together at the peripheral edges of the top and bottom halves. The envelope halves can be joined to each other by an adhesive, stitching, melting or ultra-sonic welding. Once the peripheral edges of the top and bottom halves 11A and 11B are joined together, they form a substantially water-proof container that is also RF-signal permeable, i.e., radio frequency signals can pass through the envelope 11.

The circuit board 24 in FIGS. 3A and 3B is mounted to the substrate 16 and located immediately adjacent to the sensor 100. It carries active electronic devices 25 described below. The electronic devices 25 are electrically connected to the panels 12 and 14 via connection wires 26 that are soldered to corresponding panels 12 and 14 or tack welded or fastened using conductive adhesives.

In some embodiments, electric power is provided to the electronic devices 25 and electrical/electronic signals from the devices 25 are carried over dual-function signal leads 28 that extend along the length of the panels 12 and 14 to an electrical connection cable 22. In the embodiment shown in FIGS. 3A and 3B, the connection cable 22 is located away from the circuit board 24. In an alternate embodiment, however, the cable 22 is located at the opposite end of the sleeve 11, i.e., next to the circuit board. In yet another embodiment, a battery is sealed inside the envelope 11 and connected to the electronic devices via the connection wires 26.

FIG. 4A is a perspective view of a first alternate embodiment of a pressure sensor 102 within the envelope 11 described above and having electronic devices 25 that monitor the state of the sensor 102. FIG. 4B is a cross section taken through section lines 4B-4B. FIG. 4B shows that the electronic devices 25 are mounted to a circuit board 24 that is itself mounted within a void 40 formed between two opposing sensor panels 32 and 36, which are also separated from each other by spacers 13 and 15 that are not shown in the figure for clarity.

Similar to the sensor 100 shown in FIGS. 3A and 3B, the sensor 102 shown in FIGS. 4A and 4B is comprised of a first, elongated thin, flat narrow and conductive top panel identified by reference numeral 32 albeit without a fulcrum wire making the sensor 102, and other sensors described herein as not having a fulcrum wire, suited for use as a floor mat sensor, i.e., to detect the presence or absence of a person or an object on the sensor 102, a resistance sensor or a capacitance sensor.

The top panel 32 of the embodiment shown in FIGS. 4A and 4B includes an offset portion 33 formed by a double bend 34 and which deflects upwardly and away from the bottom panel 36. The bottom panel 36 has a complementary-shaped double bend 38 and a second offset portion 35. The dual or "mirror image" offset portions 33 and 35 define a relatively large pocket or void 40 between the top and bottom panels 31 and 36. The bends 34 and 38 in the panels 32 and 36 are configured such that the void 40 between the offset portions 33 and 35 has a vertical height that is able to receive the aforementioned circuit board 24 within the void 40 as well as electronic devices 25 mounted to the circuit board 24. In embodiments that mount the circuit board to a conductive panel an insulator is preferably placed between the circuit board and conductive surfaces of the panels to prevent the conductive panels from short-circuiting exposed connections on the circuit board. Unlike the sensor 100 depicted in FIGS. 3A and 3B, the sensor 102 in FIGS. 4A and 4B is not mounted to a substrate. The pressure sensor 102 FIGS. 4A and 4B is therefore usable as a floor mat as well as a chair or bed sensor but is preferably used on rigid surfaces with the two panels 32 and 36 contacting each other when they are urged together by a force normal to them.

FIGS. 5A and 5B depict yet another embodiment of a pressure sensor 104 and electronic devices 25 mounted on a printed circuit board 24 contained within an envelope 11. In FIGS. 5A and 5B, the conductive panels forming the sensor 104 include a top panel 32 having a double bend 34 and an offset portion 33 and a bottom panel 14. As with the other embodiments, the panels are separated from each other by spacers, not shown in the figures for clarity. In FIGS. 5A and 5B, the bottom panel 14 is flat and rests on a fulcrum wire 20. The sensor 104 and fulcrum wire sit on top of a substrate 16.

The double bend or elbow 34 in the top panel is at an angle and has a length sufficient to define a void 40 that can accept the circuit board 24 and electronic components 25 mounted thereon. Small gauge wires 26 connect circuitry 25 on the circuit board 24 to the top panel 32 and the bottom panel 14 and bottom panels respectively. Electric power is provided to the devices 25 and signals from them are carried over connection leads 28.

FIGS. 6A and 6B show yet another embodiment of a pressure sensor 106. In FIGS. 6A and 6B, the circuit board 24 and its electronic devices 25 are mounted on top of, i.e., on the second side 12A of the top panel 12, with a non-conductive insulator (not shown) between them. Connection wires 26 extend from the circuit board 24 to the top panel 12 and bottom panel 14. As with the other embodiments, the panels, circuit board and connection wires are contained within the aforementioned envelope 11.

Figure 7A:
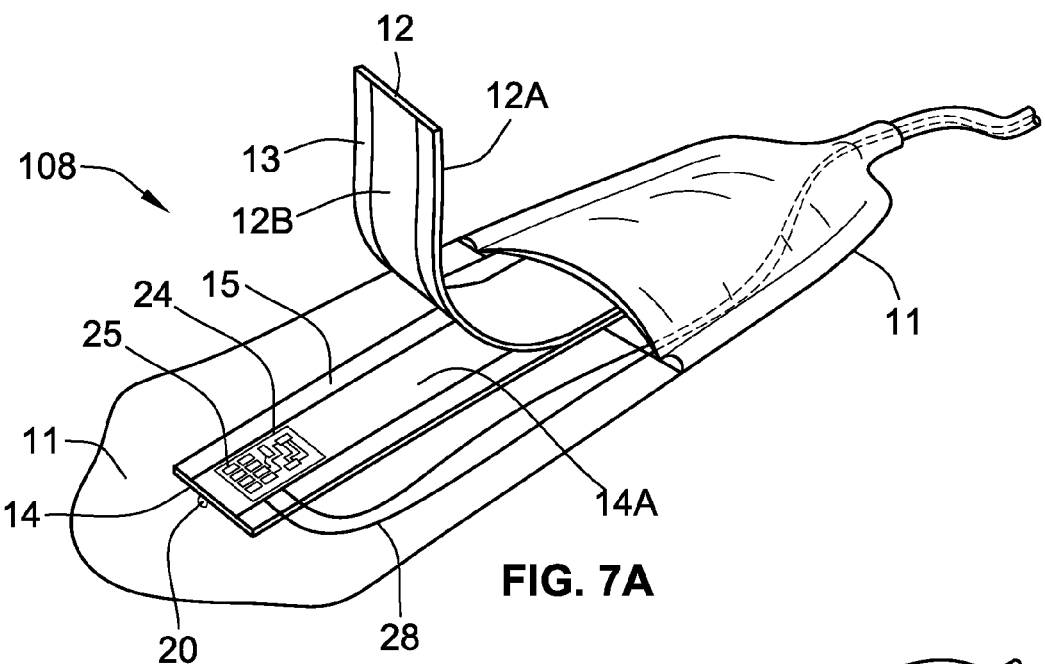
FIGS. 7A, 7B and 7C depict alternative embodiments of a pressure sensor provided with an electronic device.
Figure 7B:
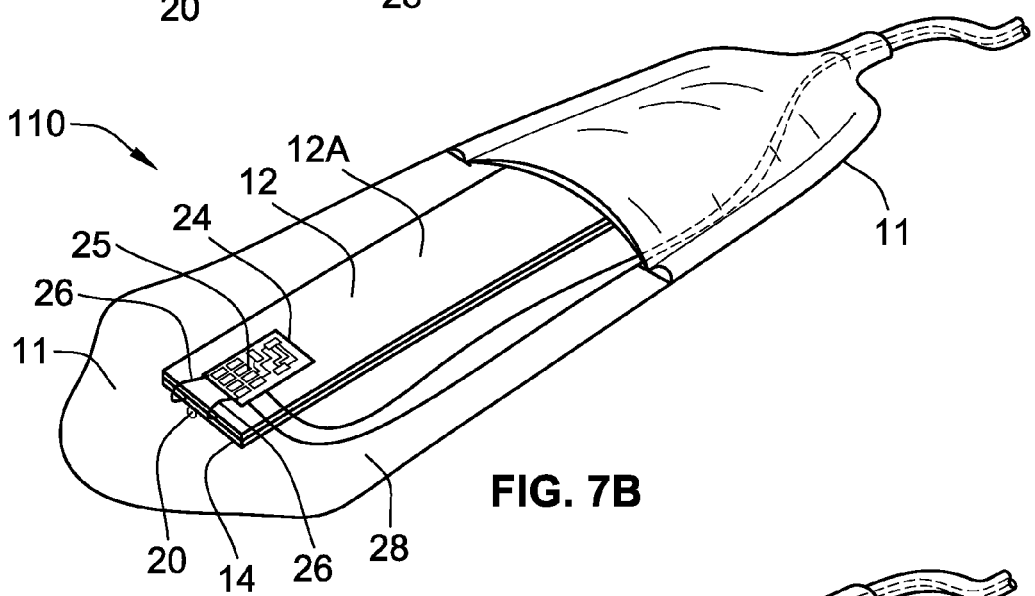
Figure 7C:
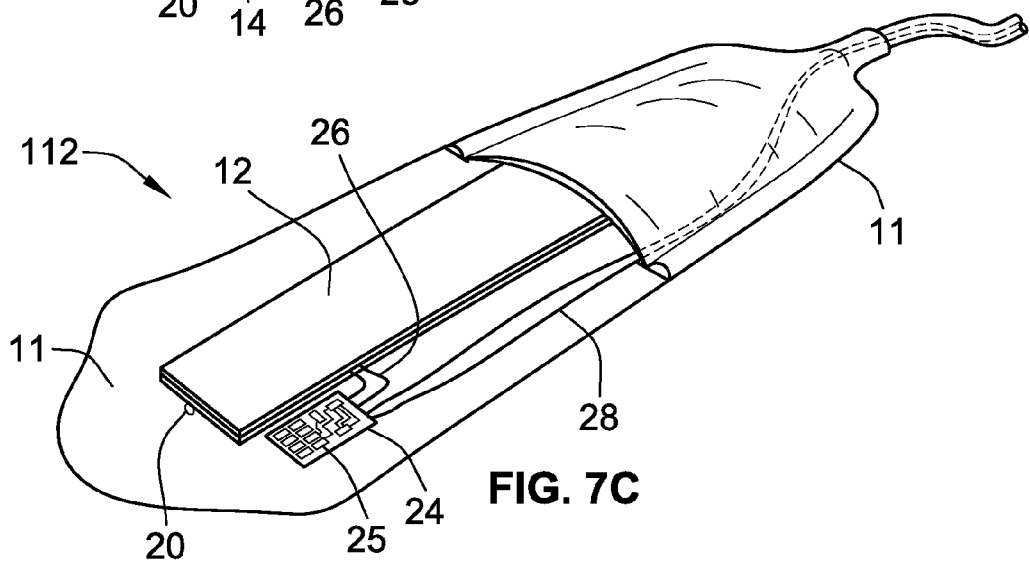

FIGS. 7A, 7B and 7C are perspective views of three more alternate embodiments of pressure sensors 108, 110 and 112 with electronic devices included within the aforementioned protective envelope 11, but which do not have or use a substrate. Each of the embodiments shown in FIGS. 7A, 7B and 7C is comprised of a top panel 12 and a bottom panel 14 however, the panels are not mounted on a substrate. In FIG. 7A, the circuit board 24 and its electronic devices are mounted in a space between the panels 12 and 14 defined by the thickness of the spacers 13 and 15. The circuit board 24 is mounted to the top or first side 14A of the bottom panel 14, however, an alternate and equivalent embodiment has the circuit board attached to the bottom side 12B of the top panel 12. A fulcrum wire 20 which runs the length of the bottom panel 14.

In the pressure sensor 110 shown in FIG. 7B, the circuit board 24 is mounted on the first or top side 12A of the top panel 12, with a non-conductive spacer or insulator between the circuit board 24 and the top side 12A of the top panel 12. In FIG. 7C the circuit board "floats" near the sensor 112 and is connected to the panels 12 and 14 by connection wires 26.

Figure 8A:
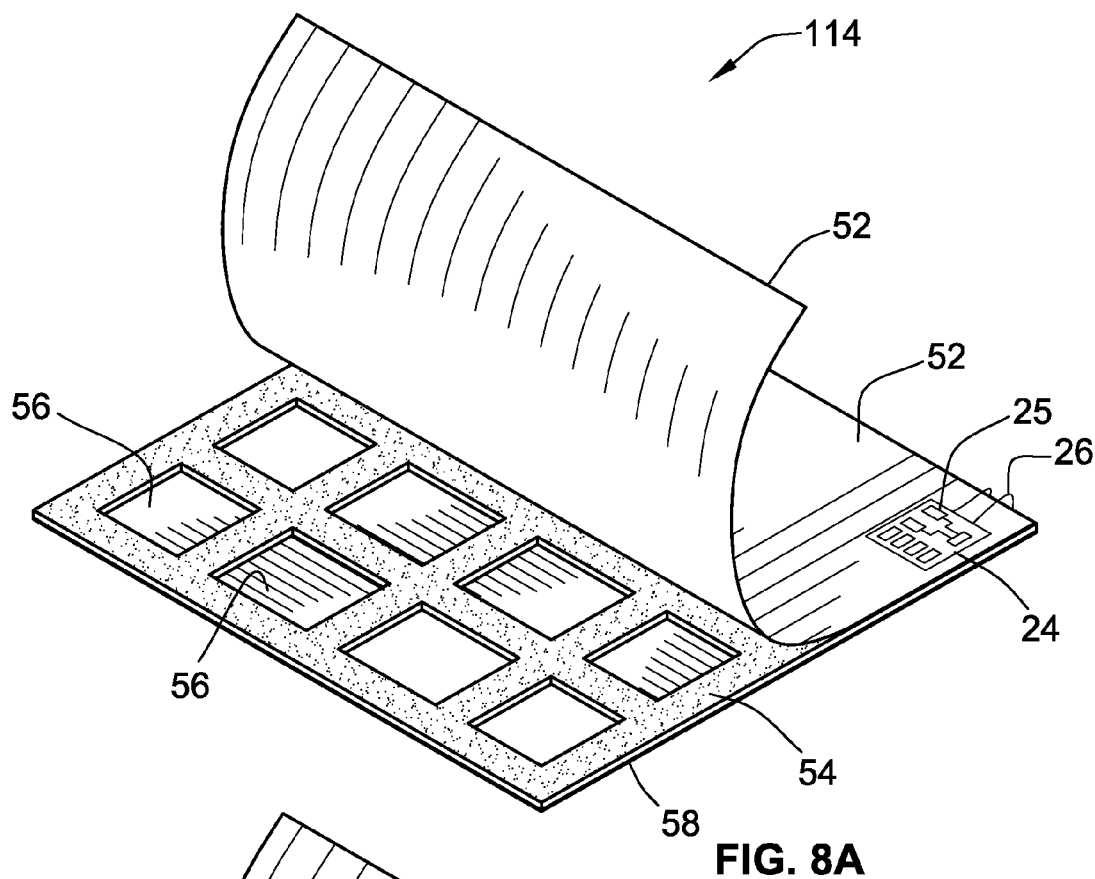
FIG. 8A is a perspective and partially exploded view of yet another embodiment of a pressure sensor provided with an electronic device.
Figure 8B:
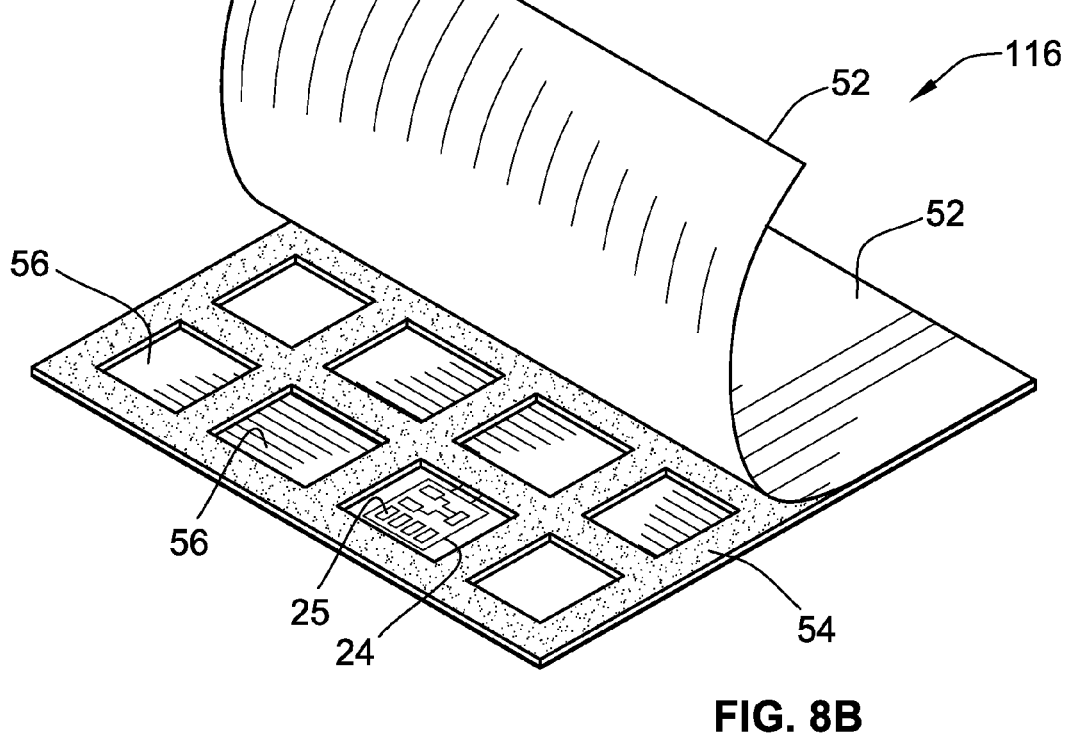
FIG. 8B is another embodiment of the device shown in FIG. 8A.

FIGS. 8A and 8B show two "chair" pressure sensors 114 and 116, which are also comprised of parallel, substantially rectangular conductive panels 52 and 58. The panels 52 and 58 are separated from each other by a non-conductive pliable gasket 54. As can be seen in the figures, the gasket 54 is formed to include numerous regularly spaced-apart, square open areas 56. A force applied to either side of the panels of the sensors 114 and 116 will cause the panels 52 and 58 to compress the gasket 54, deform and make electrical and mechanical contact with the opposite panel thereby effectively acting as a switch. The sensors 114 and 116 are both sealed into an envelope (not shown) as described above but with a shape corresponding to the shape of the panels 52 and 58.

In FIG. 8A, a circuit board 24 including electronic devices 25 that monitor the panels 52 and 58 is mounted on the top or upper surface of the top or upper panel 52. Connection wires 26 connect components on the circuit board 24 to the respective panels 52 and 58. In FIG. 8B, the gasket 54 is sufficiently thick to define a volume between the panels 52 and 58 that is able to receive a circuit board 24 with its electronic devices 25, within one of the aforementioned squares 56.

In each of the embodiments shown in FIGS. 3A-8B, the inclusion of a electronic devices 25 on, between or immediately adjacent the panels of a pressure-sensitive switch/sensor enclosed within a flexible, sealed, RF-signal transmissive/permeable sleeve or envelope 11 imbues the resulting device with capabilities that are not realized by prior art sensors. In various embodiments, the electronic devices 25 include: a processor or microprocessor; a semiconductor memory device for storing program instructions and/or data; capacitance converters and/or resistance converters; a visible indicator, such as a light emitting diode; a temperature sensor such as a thermistor; and an accelerometer, a microphone, a piezoelectric device to detect vibration, or a piezoresistive device mechanically attached to one or both of the panels to detect deformation or stress on one or both of the panels. In other embodiments, wireless transmitters are also provided within the envelope to enable the status of the sensor and information detected by other electronic devices to be wirelessly transmitted to a nearby receiver for relay to a monitoring station.

Electronic devices 25 within the envelop 11 detect moisture or liquid inside the envelope 11, corrosion or oxidation of electrical connections, an elevated temperature of either a person or the room. A person's weight can also be estimated. The time that a person has been out of bed, in bed, or lying in the same position can be determined. A bed elevation angle can be measured and a chair can be determined to be upright or lying on its side.

When used in a patient-monitoring system, the inclusion of wireless data transmission circuitry on the circuit board 24, such as an I.E.E.E. (Institute of Electronics and Electrical Engineers) 802.11-compliant "WI-FI" transmitter, or an 802.15-compliant "Bluetooth" transmitter or an Industrial, Scientific or Medical (ISM) band transmitter (amplitude or frequency-modulated) enables the transmission of sensor data to a nearby receiver (WI-FI, Bluetooth or ISM), which simplifies the implementation, operation, reliability and maintenance of a wireless patient monitoring system.

In one embodiment of the pressure sensors described above, the circuit board 24 carries a microprocessor or microcontroller having either on-chip memory or an external, i.e., separate semi-conductor memory device, which stores program instructions. When the program instructions are executed by the processor, they cause the processor to detect or monitor the state of the pressure sensor, e.g., detect whether the sensor panels are electrically contacting each other. When the program instructions are executed, the processor senses electrical contact closure (or opening) between the upper and lower panels and thereafter generates an output signal indicative of the pressure switch actuation but only after a programmable length of time has elapsed, e.g., 3 seconds.

Single-chip processors such as the PIC10F200 processor made by Microchip Technology Inc. are well-known to those of ordinary skill in the electronics arts. The processor can be programmed to consider a sensor activation to be when the panels open or close but in either case, wait a fixed amount of time before generating a signal (active high or active low) to indicates actuation of the pressure switch. When used as a bed or mattress sensor. Waiting a short period of time before determining that the sensor has closed thus avoids false "positives" as will happen when someone moves around while sleeping or when moving around. Time-delaying a signal from a pressure sensor thus avoids sending sensor activation signals caused by a person shifting or moving around in a bed or chair and not actually leaving or entering. Delaying the transmission of an indication to other circuitry and systems that form part of a patient monitoring system can avoid sending a false alert signal to a care giver.

In another embodiment, a capacitance converter embodied as an Analog Devices, Inc. AD 7150 is able to measure the capacitance between the two panels. Since capacitance between the two panels will be affected by the panel spacing or separation distance as well as the dielectric between them, measuring capacitance of the panels can thus indirectly measure an object's presence above the sensor, or a person's weight, or detect the presence of a foreign object above the sensor or the presence of someone or something other than a particular person who is expected or supposed to be sitting in a chair or lying on a mattress.

In embodiments using a capacitance converter on the circuit board 24, the capacitance sensor outputs a serial bit stream or a parallel digital word that is representative of, or proportional to the capacitance between the two panels. The serial or parallel data is received by a processor, which is coupled to radio transmitter and which is programmed to cause the transmitter to periodically broadcast a signal carrying information that corresponds to or which represents the capacitance of the two panels are determined by the capacitance converter.

In another embodiment, the circuit board 24 is provided with a light emitting diode (LED) or an incandescent bulb that acts as a visible indicator of the activity of an on-board processor and/or the sensor being open (or closed).

In yet another embodiment, the circuit board 24 supports a resistance converter, such as a Microchip PIC10F220. Measuring the resistance and generating a serial bit stream or parallel digital data word indicative of the resistance between the two panels can indicate corrosion on the surfaces of the panels facing each other or other degradation of the sensor. Resistance between the panels will also indicate the presence of conductive liquid within the envelope 11. Measuring resistance between the panels thus facilitates the detection of liquids and/or vapors inside the envelope 11.

In another embodiment, the circuit board 24 is provided with a thermistor, which is a temperature-dependent resistance and which is coupled to a processor on the circuit board 24. A thermistor can thus be used to determine whether the room temperature is too high or too low or if a person is lying in bed or chair, of if a person in the bed or chair has an elevated body temperature.

In yet another embodiment, the circuit board 24 includes an accelerometer such as an ADIS 16203 made by Analog Devices, which can indicate the spatial orientation of the sensor and a person or object it is attached to. When used as chair sensor, the accelerometer can indicate whether the chair has fallen over or is about to tip over. When used with a mattress sensor, the accelerometer can indicate whether the mattress/bed is inclined or declined. It can also indicate the degree to which the sensor is inclined and thus provide an indication of a person's weight vis-a-vis the support provided by a bed and in that sense, whether a mattress/bed is providing adequate or appropriate support for a patient based on a detected/measured angle of a sensor.

Other embodiments use electronic circuits that measure inductance, the intensity of light impinging on the outside of the envelope 18 or the circuit board 24 as well as the wave length of such incident light.

The detection of a sensor panels opening and closing, and the detection/measurement of capacitance, resistance, inclination angle, temperature, inductance or the like, if of limited value if that information is not conveyed so that it can be used. In various embodiments of the invention disclosed and claimed herein, and as set forth above, information obtained from the sensor panels can be transferred via a hard-wired connection that is made via the connection cable 22 depicted in the figures. In other preferred embodiments, the circuit board 24 is provided with circuitry to implement an IEEE (Institute of Electrical and Electronic Engineers) 802.15 or "Bluetooth"-compliant transmitter. In yet other embodiments, the circuit board 24 includes electronics to implement an I.E.E.E. 802.11(a), (b), (g) or (n)-compliant transmitter or an ISM-band transmitter. In yet other embodiments, a ZigBee® compliant transmitter is used. ZigBee® is a specification for communication protocols that use small, low-power digital radios that are based on the IEEE 802.15.4 standard for wireless personal area networks or (WPANs). Regardless of the protocol or technology, radio transmitters within the envelope 11 can wirelessly transmit signals carrying data representative of the various aforementioned physical characteristics, to a corresponding receiver (WI-FI, Bluetooth, Zigbee® or ISM) thereby enabling a wireless patient monitoring system/wireless sensor monitoring system.

Figure 9:
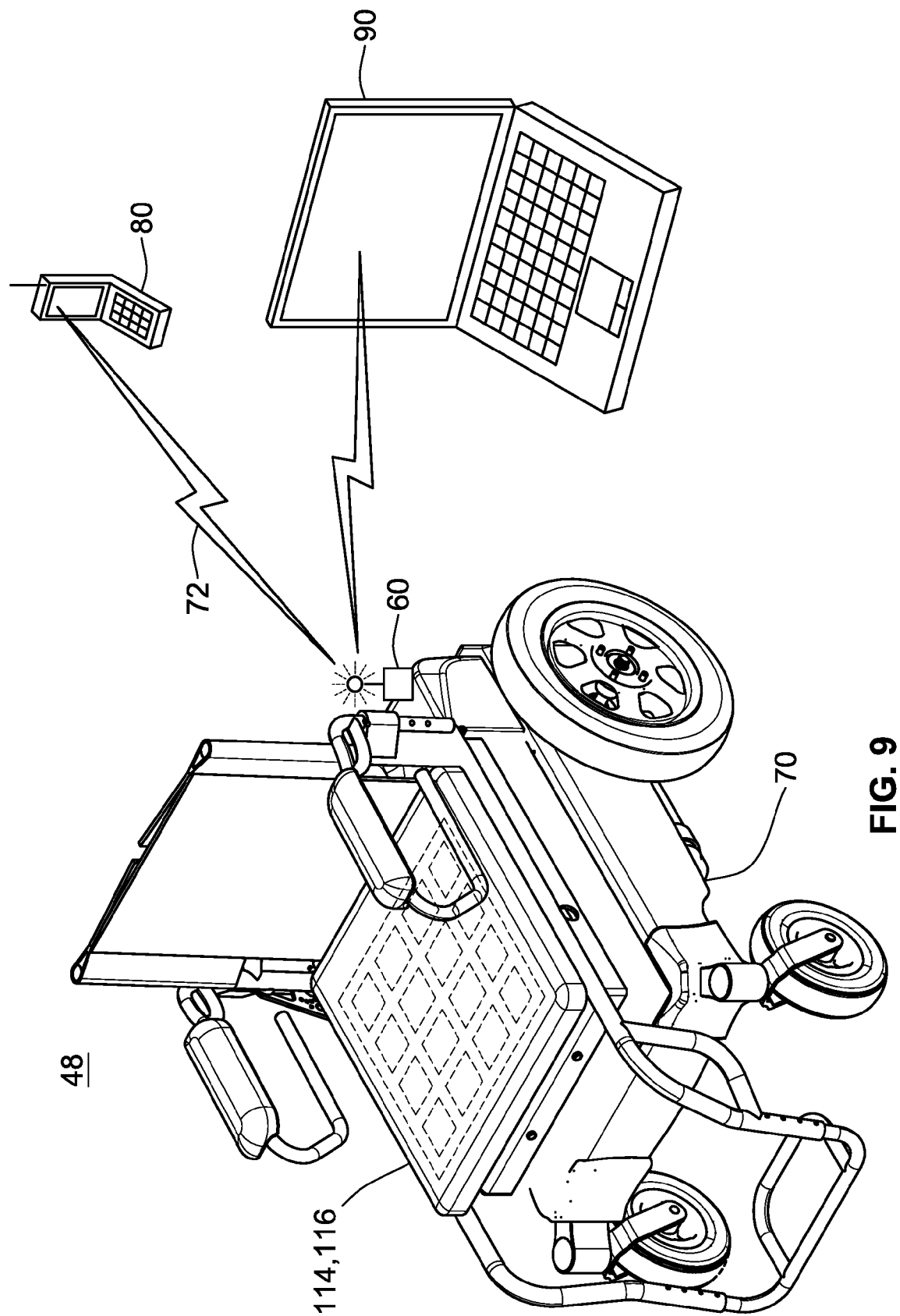
FIG. 9 depicts a patient monitoring system using one of the pressure sensors depicted in FIGS. 8A and 8B.

FIG. 9 shows a block diagram of one embodiment of a patient-monitoring system that uses one or more of the sensors 114, 116 shown in FIGS. 8A and 8B installed on a wheelchair 70, and one or more of the electronic devices described above. In FIG. 9, the weight of a person sitting in the chair 70 will activate one of the sensors 114, 116. When the person leaves the chair, the person's departure or removal from the chair can be detected as described above and wirelessly transmitted to a remotely-located monitoring station. By adding sensors such as an accelerometer, capacitance or resistance detector or a thermistor to the sensors 114 or 116, it then becomes possible to respectively detect whether the chair is upright or whether there is liquid or moisture in the sensor and, likely in the chair as well or measure patient or room temperature.

Other sensors added to the circuit board or otherwise placed in or on the envelope include one or more microphones, which enable the detection of sounds in a person's room or emanating from a person and piezoelectric and piezoresistive sensors attached directly to the panels can detect vibration of the sensor and/or mechanical stress.

In FIG. 9, as well as the other figures, sensor activation and/or other measurable state or state change or information from an electronic device or sensor is conveyed to a patient monitoring system (not shown) via a signal 72 transmitted from a either Bluetooth, cellular, WI-FI (802.11) or other radio transmitter identified in FIG. 9 by reference numeral 60. The transmitted signal is received by a corresponding receiver, e.g., a cell phone 80 or computer 90 equipped with a Bluetooth, WI-FI or Zigbee®-compliant receiver.

In one embodiment, the transmitter 60 is a separate device that is connected to the chair sensor 114, 116 using a cable as shown. In another preferred embodiment, the transmitter 60 is mounted on the aforementioned circuit board 24 within an envelope 11 as described above and which forms part of the sensor 114, 116 as shown in FIGS. 3A-8B.

A radio signal, identified by reference numeral 72 is transmitted to either a cell phone 80 or a computer 90 having a receiver compatible with the transmitter. The cell phone 80 and the computer 90 are configured to forward information received from the sensor 50, to a health care provider, family member or other person, using conventional and well-known data transfer methodologies. Data received by a cell phone or portable data terminal device can be transmitted from the cell phone or portable data terminal device using an SMS (short message service) or "text" message or an e-mail. "Data" transmitted from the cell phone or portable data terminal device can also include a pre-recorded telephone message, stored in the cell phone of data terminal device and sent from the device as a telephone call routed over the public switched telephone network (PSTN) or as a voice-over-Internet-protocol (VOIP) call.

Figure 10B:
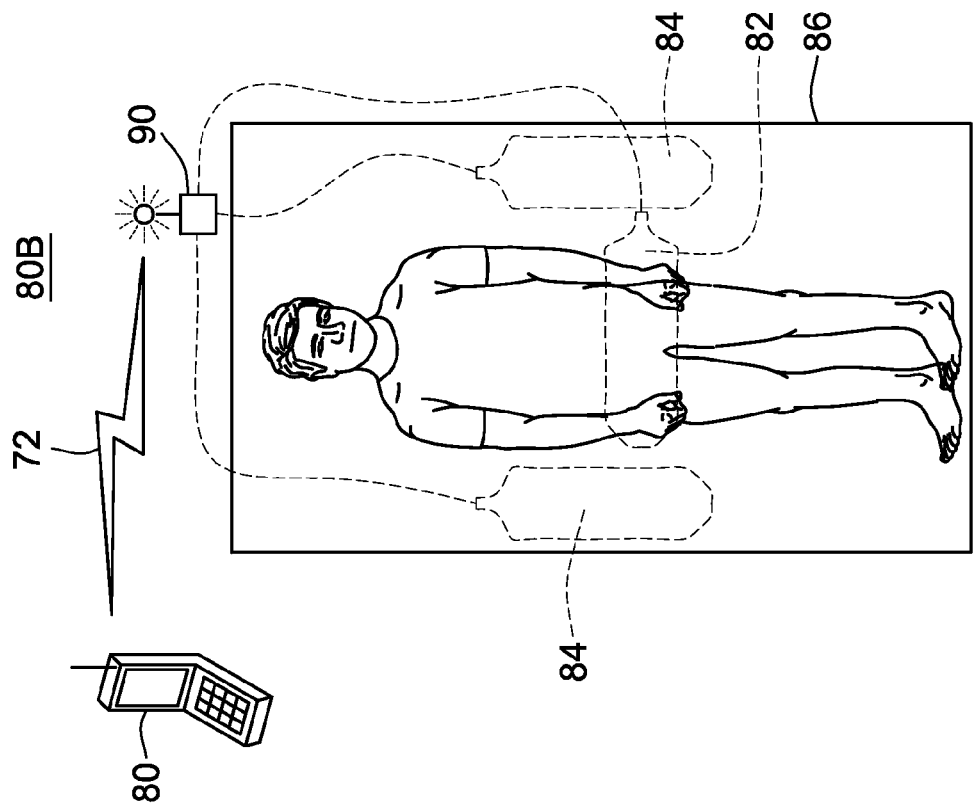
FIGS. 10A and 10B depict patient monitoring systems using one or more of the pressure sensors depicted in FIGS. 3-8 inclusive.
Figure 10A:
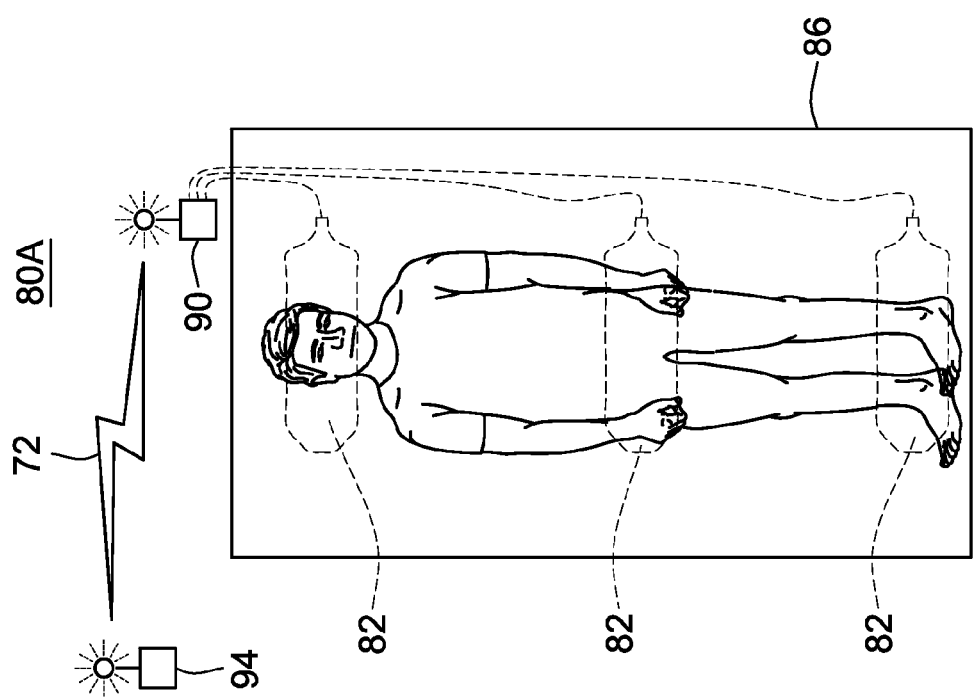

FIGS. 10A and 10B show alternate embodiments of patient monitoring systems that use one or more of the sensors described above and depicted in FIGS. 3A-8B. In FIGS. 10A and 10B, transverse sensors 82 under the mattress 86 output signals in response to a person lying on the mattress 86. The sensors 82 can thus be used to indicate the presence or absence of a person lying on the mattress 86 as well as the length of time that a person has been lying in a particular position. The transverse sensors 82 can also be provided to the mattress, which are constructed to include other electronic devices, such as the aforementioned sensors that include a capacitance sensor, a resistance sensor, a thermistor and/or an accelerometer, a microphone, a piezoresistive or a piezoelectric sensor.

In FIG. 10B, two patient longitudinal sensors identified by reference numeral 84 are actuated when the patient is close to the edge of the mattress 86 or when a person first gets into or out of bed. As with the transverse sensors 82 of FIG. 10, the longitudinal sensors 84 can also be provided with other electronic devices that include the aforementioned capacitance sensor, resistance sensor, thermistor and/or an accelerometer.

Actuation or de-actuation of one or more of the sensors, as well as information obtained by other electronic devices listed above, is detected and/or received by the CPU and wirelessly transmitted from a transmitter 90, which can be either a separate transmitter device connected to a sensor via a cable as shown in FIGS. 9 and 10A and 10B, or mounted within and as part of the sensors as described below.

Figure 11:
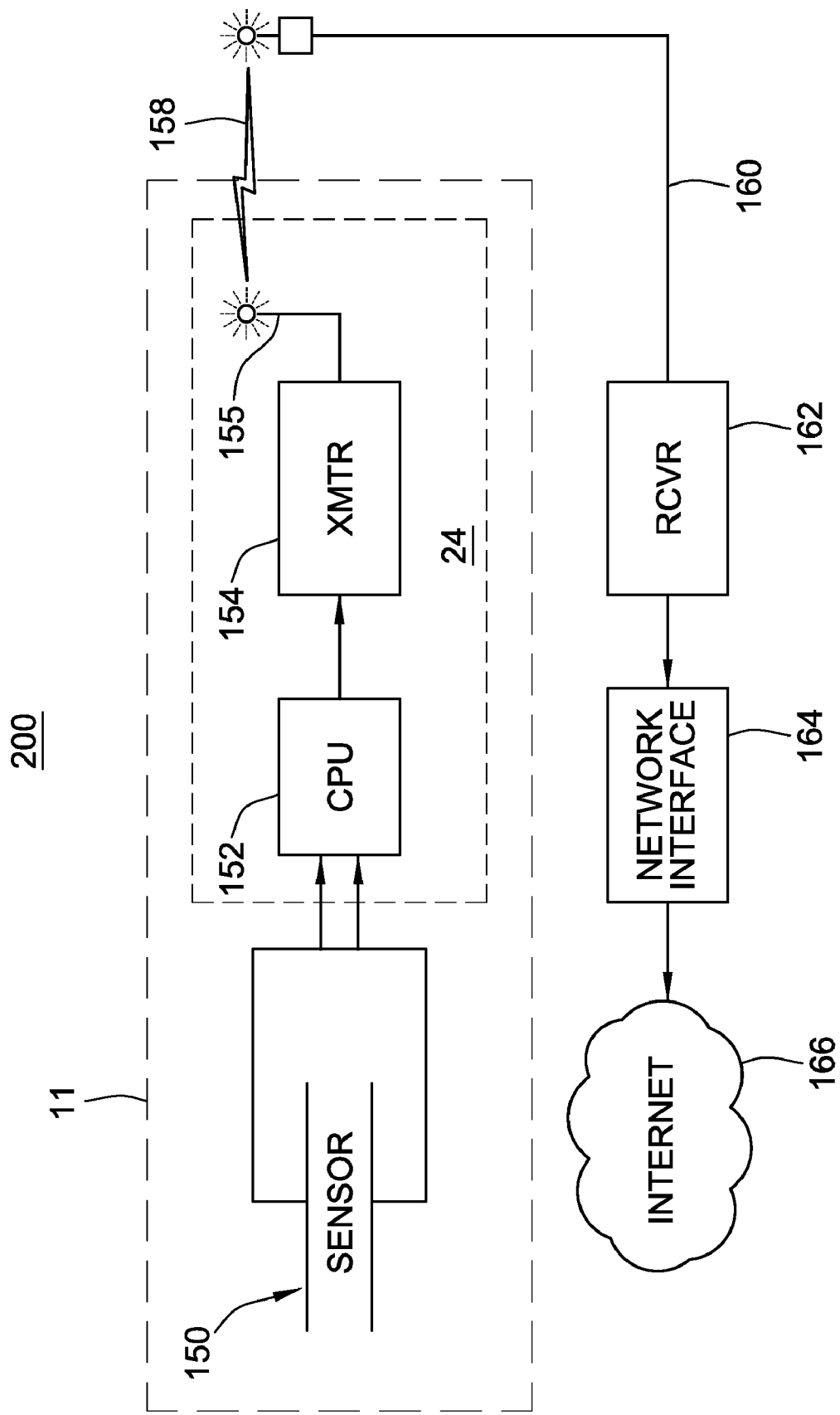
FIG. 11 is a block diagram of a remote patient monitoring system using a sensor and electronics depicted in FIGS. 3A-8B.

FIG. 11 is a block diagram of a remote patient monitoring system 200 utilizing at least one of the pressure sensors described above, which have various electronic devices mounted on the circuit board 24 that accompany the sensor inside the aforementioned protective envelope 11. For simplicity and brevity, reference numeral 150 identifies any one or more of the sensors depicted in FIGS. 3A-8B and which are identified in those figures by reference numerals 100, 102, 104, 106, 108, 110, 112, 114 and 116. In FIG. 11, a sensor 150 is electrically coupled to a processor/CPU 152, which is itself coupled to a transmitter 154. The CPU 152 and transmitter 154 are mounted on a circuit board 24. The sensor 150 and the electronic devices 152 and 154 are enclosed together within the protective envelope 11.

A power supply for the electronic devices but which is not shown for simplicity, can be embodied as either an enclosed battery or an external power supply supplied via the connection cable 22 or one that is electrically connected to the electronic devices by a through-the-envelope 11 connector not shown. The envelope 11 and its contents, i.e., the sensor 150 and electronic devices thus comprise a self-contained, patient monitoring station for either a chair or mattress.

The processor/CPU 152 operates according to program instructions that are stored on either the same semiconductor substrate as is the processor/CPU or which are stored in a separate memory device that is also mounted on the circuit board 24 but which is not shown for clarity and brevity. Such memory devices are well known to those of ordinary skill in the computer arts.

For brevity, a sensor 150 that changes state, e.g., opens or closes, or which detects or measures a capacitance, resistance, spatial orientation, vibration, sound, resistance, stress, temperature, or other measurable or detected condition is considered herein to undergo a change of state or "state change." When a sensor 150 undergoes a state change, the state change is conveyed to the processor 152, which in turn detects the state change (or information included therein) and generates a digital output signal, i.e., a serial bit stream or a digital word, representative of the detected state change and which is input to the transmitter 154.

The transmitter 154, which is preferably embodied as either a Bluetooth, WI-FI or perhaps a Zigbee®-compliant radio frequency transmitter, broadcasts a corresponding signal 158 to a nearby receiver 162 via one or more antennae 155. Other transmitters that can be used include an amplitude or frequency modulated transmitter configured to operate in the Industrial, Scientific and Medical (ISM) band. The signal 158 broadcast from the antenna therefore carries sensor-generated information, as well as a unique identity of the transmitter 154 to a receiver 162. Upon reception of the signal 158, a receiver 162 demodulates the signal 158 to recover the identity of the transmitter that sent the signal 158 and thereby associate the sensor information with the corresponding transmitter that sent it. The receiver 162 thereafter generates its own output signal, which is coupled to a network, such as the Internet 166, via a network interface 164.

The identity broadcast by the transmitter 154 uniquely associates a transmitter 154 with a sensor 150 or sensors and thereby enables multiple transmitters to be used within an environment where there might be multiple transmitters the broadcast signals of which are received by one or more of the same receivers. The network interface 164 generates a data message compliant with the network 166, and which can include the transmitter identity, all of which can then be routed by the network 166 to a remotely-located monitoring station (not shown) where the transmitter identity can be recovered and corresponding sensor data acted upon.

Figure 12:
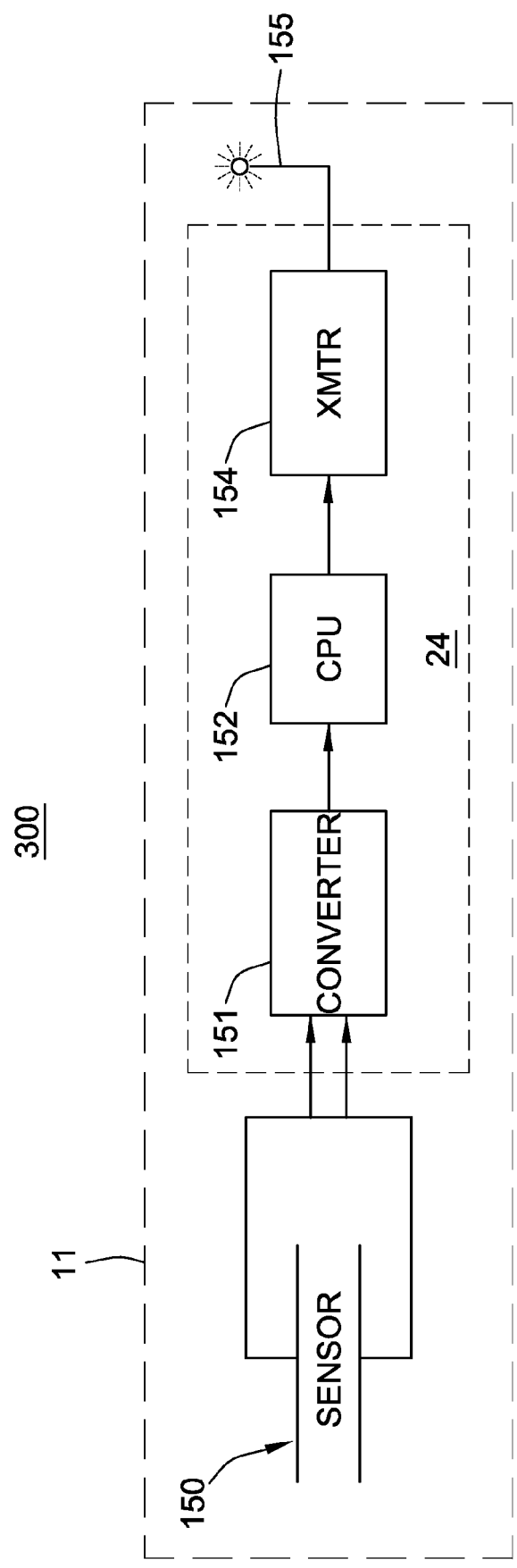
FIG. 12 is a block diagram of an alternate embodiment of a portion of the system shown in FIG. 11.

FIG. 12 depicts part of a remote patient monitoring system shown in FIG. 11. In FIG. 12, the circuit board 24 is mounted within the envelop 11 and carries additional electronics that convert measurable characteristics of the sensor 150 into either a serial or parallel data stream. The converter 151 shown in FIG. 12 can be embodied as one or more of the aforementioned sensors, such as a capacitance sensor, a resistance sensor, temperature sensor, inductance sensor, microphone, vibration sensor, piezoelectric or piezoresistive sensor, or an accelerometer that senses the spatial orientation of the sensor 150.

A state change or output signal from the converter 151 is coupled into the CPU 152. The CPU 152 receives signals/data from the converter 151 and generates an output message or signal representative of the condition sensed or detected by the converter 151. The message output from the CPU is provided to the transmitter 154, which broadcasts a signal carrying the transmitter identity and information that represents the state change information received by the CPU from the converter 151, and ultimately the sensor 150.

The signal from the transmitter 154 is broadcast from an antenna located on either the circuit board 24 or as part of the envelope 11. The physical status or other measurable characteristic of the sensor 150 can thus be communicated to a remotely located monitoring station, all from within the envelope 11.

Figure 13:
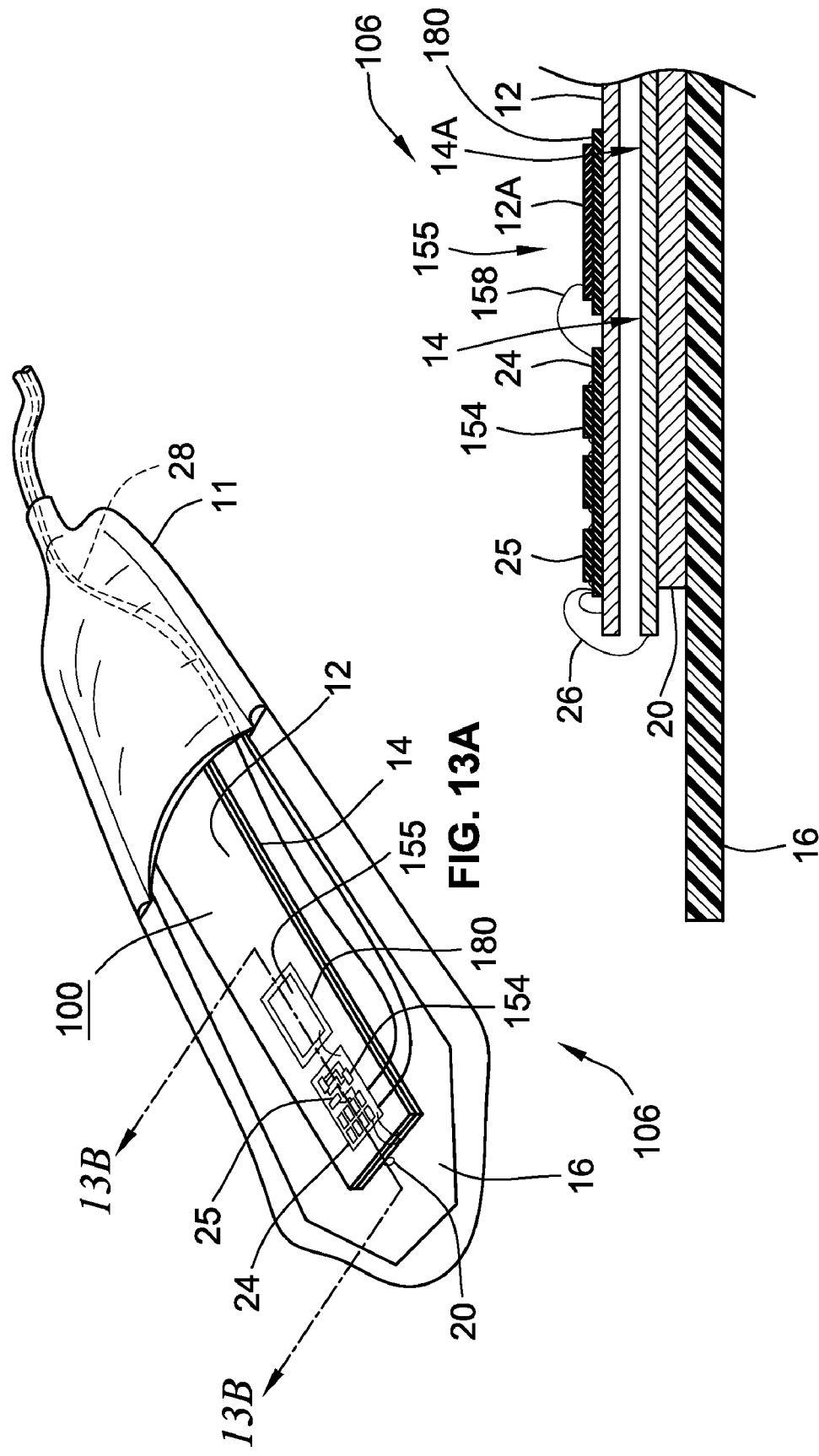
FIG. 13A is a perspective view of a sensor, electronics and a patch antenna.
FIG. 13B is a cross section taken through section lines 13A-13A.

FIG. 13A is a perspective view of a sensor 100 having electronic devices 25 mounted to a circuit board 24. FIG. 13B is a cross section of the device shown in FIG. 13A taken through section lines 13B-12B. The electronic devices 25 include at least a CPU coupled to a transmitter 154. A transmission line 158 couples the transmitter 154 to a patch antenna 155, which is mounted to a dielectric layer 180, which is attached to the top panel 12 of the sensor 100.

Patch antennas are well known to those of ordinary skill in the art as being effective radiators in a forward direction, i.e., away from the plane of the flat, conductive "patch" that forms a radio signal radiator. In addition to having a planar or substantially planar radiator attached to a dielectric, patch antennas have a ground plane "behind" the dielectric layer. Since the top panel 12 of the sensor 100 is conductive, the top panel 12 thus functions as a ground plane for the patch antenna 155.

Figure 14:
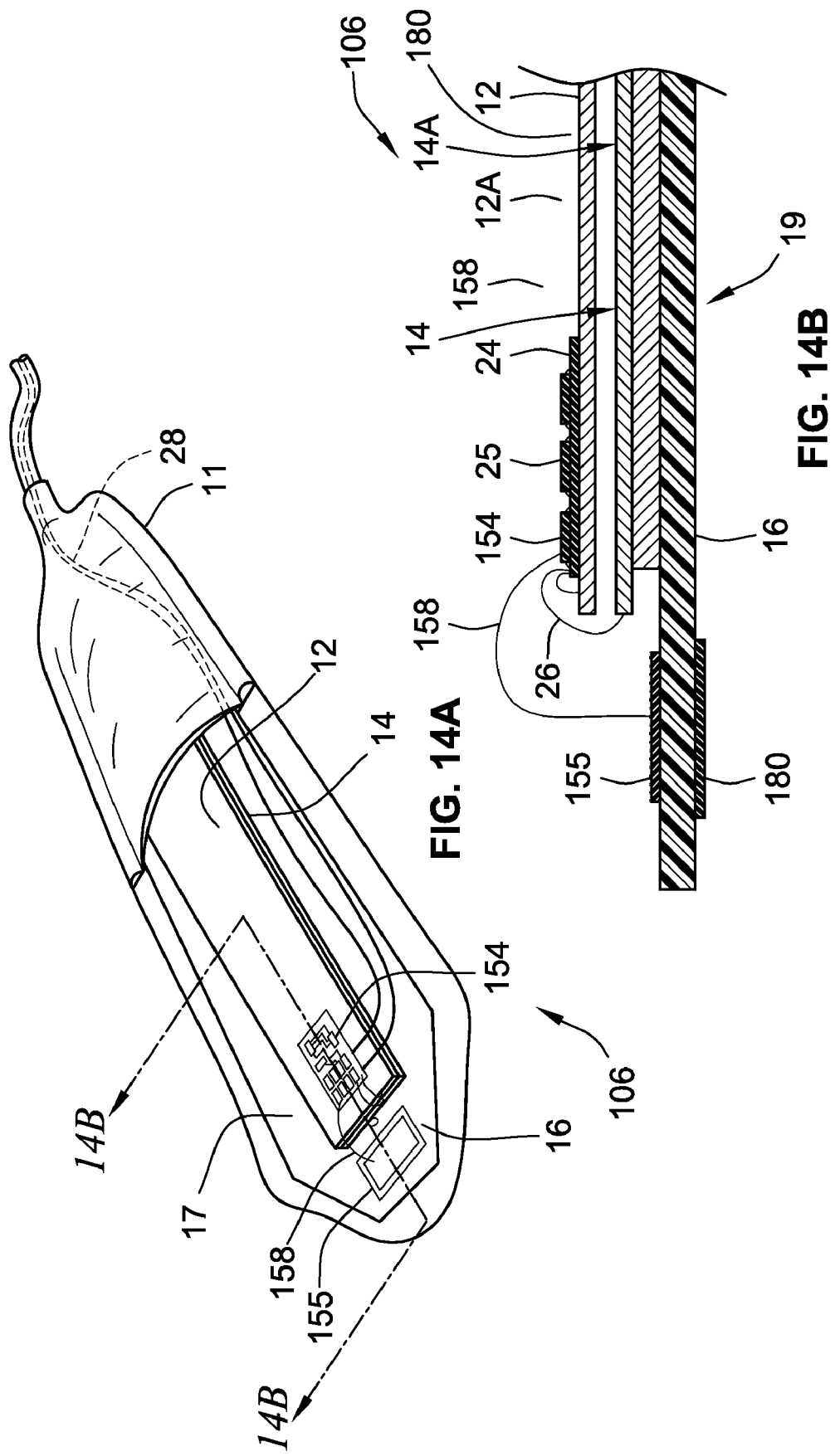
FIG. 14A is a perspective view of a sensor, electronics and an alternate embodiment of a patch antenna.
FIG. 14B is a cross section taken through section lines 14A-14A.

In another embodiment shown in FIGS. 14A and 14B, a patch antenna 155 is attached to the top surface 17 of the aforementioned substrate 16, which as described above is a plastic, i.e., dielectric material. A conductive ground plane 180 is attached to the bottom surface 19 of the substrate 16, directly underneath the patch antenna 155 and coupled to a reference potential for the transmitter 25 via a ground lead that is not shown in the figure. A transmission line 158 connects the radiating element of the patch antenna 155 to a transmitter 154 on the circuit board 24. The substrate 16 in FIGS. 14A and 14B thus forms a dielectric layer for a patch antenna 155, placed or formed directly onto the substrate 16. In another embodiment, a patch antenna having its own ground plane on opposite sides of a dielectric is attached to the top surface of the substrate such that the ground plane for the patch antenna 155 is attached to the dielectric substrate.

Figure 15:
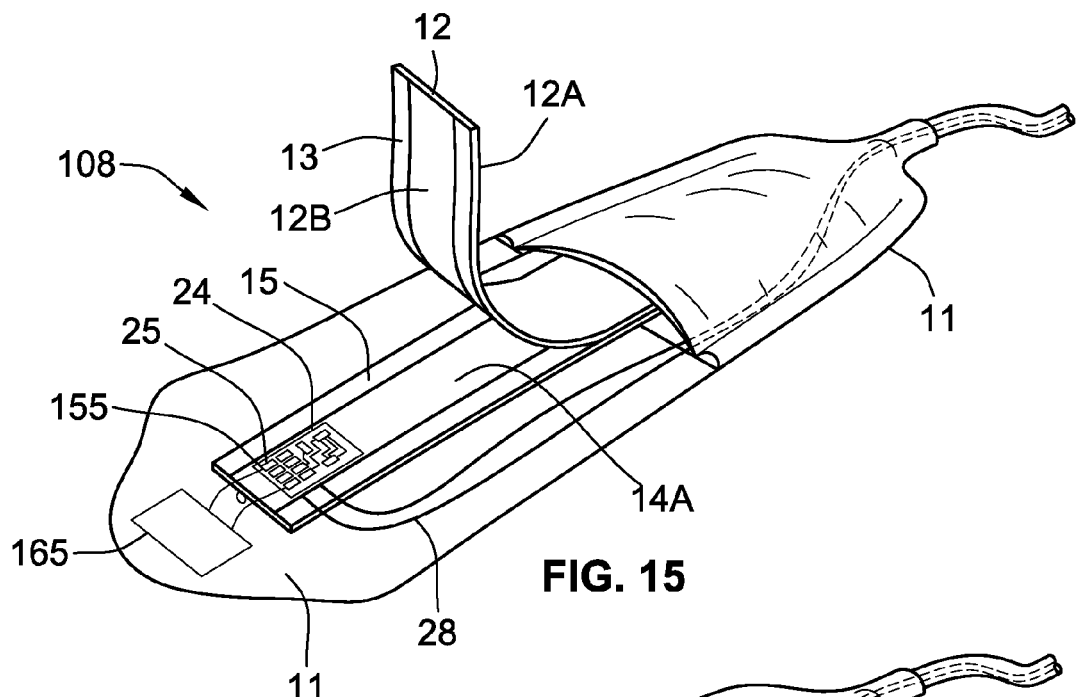
FIG. 15 shows another embodiment of a sensor with a loop antenna.

FIG. 15 shows another embodiment of one of the sensors 150 mounted within a protective envelope 11 with a circuit board 24 between the sensor panels 12 and 14 and which supports electronic devices 24 that include a radio transmitter 25. A simple loop antenna 165 extends away from the circuit board 24 and is attached to the inside surface of the envelope 11 but electrically connected to the radio transmitter 155. In an alternate embodiment, a loop antenna is provided on the circuit board 24 but not visible in the figures.

Figure 16:
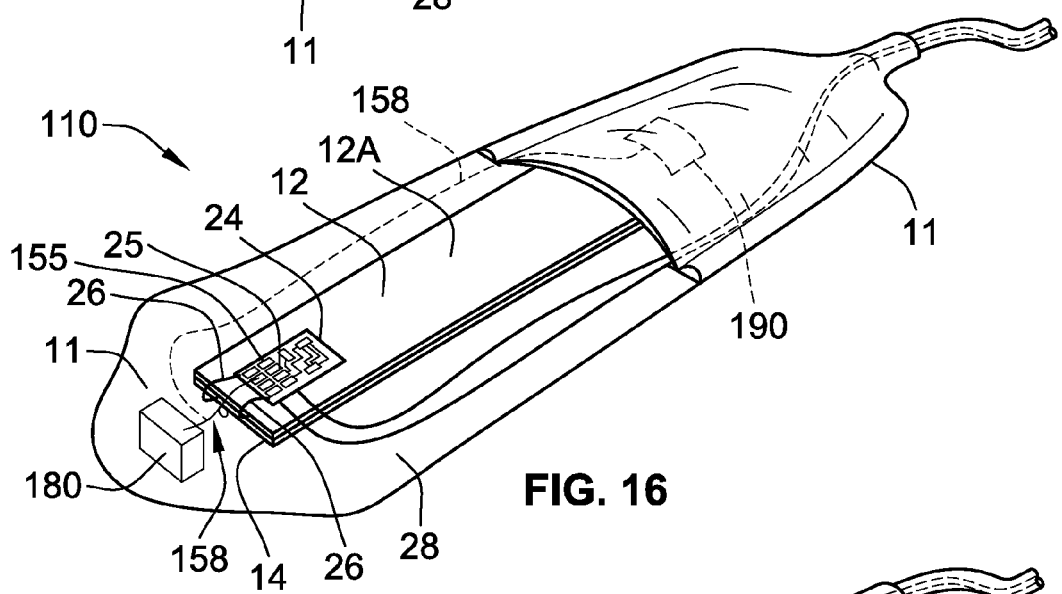
FIG. 16 shows a sensor with a fractal antenna.

FIG. 16 shows one of the sensors 150 mounted within a protective envelope 11 with a circuit board 24 mounted to the top panel 12. A three-dimensional block antenna 180 is attached to the inside surface of the envelope and connected to the radio transmitter 155 by a short transmission line 158. FIG. 16 also shows the alternate use of a fractal antenna 190 attached to either the outside surface of the envelope 11 or the inside surface of the envelope 11 as shown. A transmission line 158 extends between the transmitter 158 and the fractal antenna 190.

A fractal antenna is considered herein to be an antenna that uses a fractal or similar structure to maximize the electrical length of a conductive material that can receive or transmit radio signals within a given total surface area or volume. Fractal antennas are very compact, multiband or wideband, and are useful at cellular, Bluetooth, WI-FI and microwave frequencies. A good example of a fractal antenna is in the form of a shrunken fractal helix.

Figure 17:
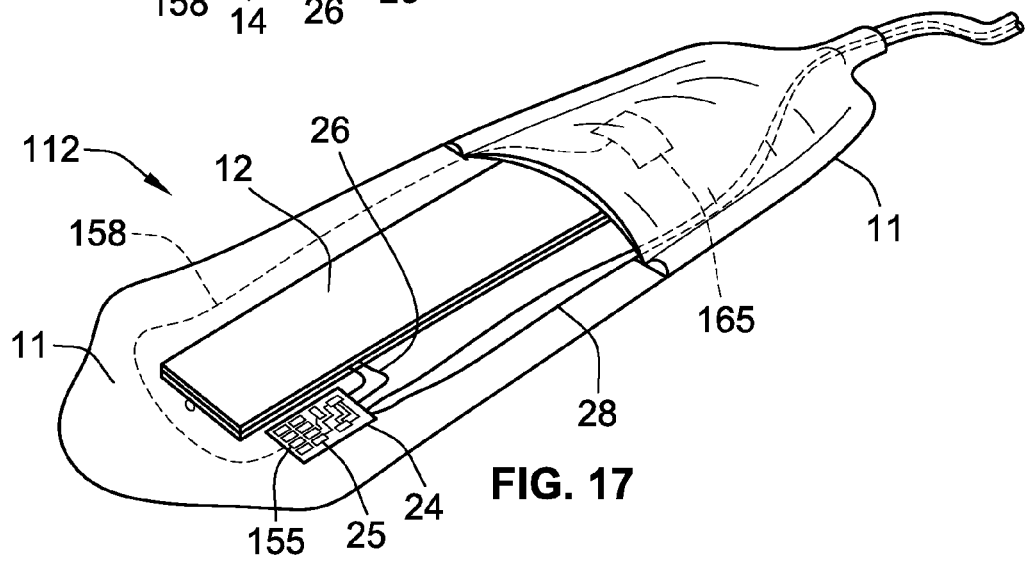
FIG. 17 shows a sensor with a loop antenna mounted to the envelope.

Finally, FIG. 17 shows one of the sensors 112 mounted within a protective envelope 11 with a circuit board 24 adjacent the sensor 150 but having a simple loop antenna 165 mounted to either the outside or inside surfaces of the envelope 11. As shown in the figures, the antenna 165 is connected to the radio transmitter 155 by a short transmission line 158.

It should be noted that there are many antennas that are effective radiators at Bluetooth, WI-FI, cellular and Zigbee® frequencies and those of ordinary skill in the art will recognize that the antennas described above are only a few of those that can be used to transducer RF energy from a transmitter. A loop antenna can be formed on the substrate 16 for the sensors, the circuit board 24, on interior or exterior surfaces of the envelope or on a dielectric layer placed on a surface of a panel 12 or 14. Fractal antennas can be formed on the envelope interior and exterior surfaces, the substrate 16 for the sensors, the circuit board 24 or another circuit board, or an a dielectric placed on a surface of a panel 12 or 14. In another embodiment, a dipole antenna (not shown but well known in the art) is used. End-fed antennas can also used and include quarter-wavelength, half or full-wavelength end-fed antennas. Those of ordinary skill will recognize that three-dimensional antennas formed of conductive panels deposited onto the surfaces of a block of dielectric material can also be used. They will also recognize that the placement of an antenna along a bed sensor is a design choice as is the placement of an antenna on a chair sensor.

Those of ordinary skill in the art will recognize that in some applications, an omni-directional antenna might be preferred in order to facilitate placement of a receiver, whereas in other applications a highly directional antenna might be preferred in order to avoid or reduce the transmission of RF signals to other receivers or to focus the limited power output from the transmitter.

As used herein, antenna, should be construed to include any structure or device capable of radiating electromagnetic energy from a transmitter, regardless of the radiation pattern that a device might have or create, regardless of where such a structure is located in, on or around a mattress or chair sensor envelope and regardless of where the transmitter is located.

For purposes of claim construction, circuit boards 24 depicted in the drawing as well as the electronic devices 25 the circuit boards carry, are considered to be mounted to the conductive panels in panel areas or regions denominated as "land" areas. By way of example, the "land" area in FIG. 5B is the area of the panel directly below the circuit board 24 as the circuit board 24 sits atop the upper surface of the lower panel 14 and within the void 40. The electronic devices 25 are thus also considered to be in, or mounted to the land area. In FIG. 6A, the "land" area is considered to be the area to which the circuit board 24 is attached to the top panel 12. In FIG. 7A, the "land" area is considered to be the surface area of the lower panel 14 to which the circuit board is attached and between the two spacers. In FIGS. 8A and 8B, the "land" area is considered to be the surface of the top panel 52 in FIG. 8A and a corresponding area to which the circuit board 24 is mounted in FIG. 8B. The embodiments shown in FIGS. 3A, 3B and 7C do not have "land" areas but instead locate the circuit board 24 off to one side of the panels on either the substrate 16 or floating within the envelope 18 as shown in FIG. 7C.

In all of the embodiments except those shown in FIGS. 8A and 8B, the panels are elongated strips, which should be construed to mean elongated rectangular strips having lengths greater than their widths. In the embodiments shown in the figures, the elongated strips preferably have thicknesses between about 0.003 and about 0.007 inches. In pressure sensor embodiments that use a fulcrum wire, the fulcrum wire is preferably made of solid steel wire having a diameter of between about 0.010 inches and about 0.025 includes. The most commonly/often-used size for the fulcrum wire is about 0.015 inches.

In order to be able to operate as a switch, it is important that panels that lie against a fulcrum wire (i.e., panels not used as, or with floor mats for instance) be sufficiently flexible to bend enough in order to make contract with the panel that is away from the fulcrum wire. In one embodiment, the top panel 12 is relatively rigid with respect to the bottom panel such that the application of a force on the top panel causes the bottom panel but not the top panel to deflect or bend around the fulcrum wire In such an embodiment, only one panel is considered to be flexible.

For purposes of reliability and longevity, surfaces of the panels can be coated with corrosion-resistant metals that include silver, gold, platinum, and in some instances, copper. Coating the panels with corrosion-resistant material increases the life span of sensors used in hostile environments, i.e. environments where the panels are subjected to corrosive materials that include body fluids and cleaning solutions, In preferred embodiments, the substrate 16 is comprised of a plastic material, examples of which include high density polyethylene (HDPE) or nylon. The sleeve 18 is preferably comprised of a flexible vinyl or a low density polyethylene.

In each of the embodiments shown, it can be seen that the sensor provides a pressure activated switch embodied as the aforementioned panels, an electronic device such as a CPU, memory device, resistance sensor, capacitance sensor, etc. an envelope 18 enclosing the switch and electronic device and one or more wires that extend through the envelope to provide a connection to an external transmitter.

The foregoing description is for purposes of illustration only. The scope of the invention is defined by the appurtenant claims.

What is claimed is:

1. A mattress or chair sensor (sensor) comprised of:
a flexible dielectric envelope that defines an interior volume and which includes therein, a sensor to detect a person on a mattress or a chair; and
a single, substantially planar, elongated plastic substrate (substrate) having first and second opposing sides, the substrate being within the interior volume of the dielectric envelope and being sized, shaped and arranged to prevent the single plastic substrate and from being driven into a mattress or chair pad by the weight of a person to be monitored;
a processor within the interior volume of the envelope;
a radio frequency transmitter within the interior volume and electrically coupled to the processor; and
an antenna within said interior volume and electrically coupled to the radio frequency transmitter, radio frequency signals broadcast from the antenna carrying sensor-generated information.

2. The mattress or chair sensor of claim 1, further comprised of first and second elongated metal strips, the metal strips having first and second elongated edges, the metal strips being electrically and spatially separated from each other by first and second non-conductive spacers located between the first and second metal strips and adjacent to the first and second elongated edges, the spacers maintaining a separation distance between the first and second metal strips and defining an open space between the elongated metal strips.

3. The mattress or chair sensor of claim 2, wherein at least one electronic device is located between the first and second elongated metal strips.

4. The mattress or chair sensor of claim 1, wherein the sensor is comprised of an accelerometer configured to indicate spatial orientation.

5. The mattress or chair sensor of claim 1, wherein the sensor is comprised of a temperature sensor.

6. The mattress or chair sensor of claim 2, wherein the sensor is comprised of a capacitance converter configured to measure capacitance between the first and second elongated metal strips and configured to output to said processor, a signal representative of said capacitance.

7. The mattress or chair sensor of claim 2, wherein the sensor is comprised of a resistance converter configured to measure electrical resistance between the first and second elongated metal strips.

8. The mattress or chair sensor of claim 1 wherein the sensor is comprised of a microphone.

9. The mattress or chair sensor of claim 1 wherein the sensor is comprised of a piezo-electric.

10. The mattress or chair sensor of claim 1 wherein the sensor is comprised of a piezo-resistive.

11. The mattress or chair sensor of claim 1 wherein the sensor is comprised of a vibration sensor.

12. The mattress or chair sensor of claim 1, wherein the antenna is formed on a surface of said substrate.

13. The mattress or chair sensor of claim 2, wherein said antenna is formed on a surface of said substrate.

14. The mattress or chair sensor of claim 1, wherein the antenna is a directional antenna.

15. The mattress or chair sensor of claim 6, wherein the capacitance converter is configured to measure a weight.

16. The mattress or chair sensor of claim 1, wherein the sensor is comprised of first and second conductive panels.

17. A sensor comprised of:
a flexible plastic dielectric envelope (envelope) having an exterior surface and an interior surface, the envelope defining an interior volume, which includes first and second substantially rectangular conductive panels separated from each other by a non-conductive pliable gasket, the gasket and panels being configured to define a plurality of open area between the panels wherein gasket material surrounds each open area;
a circuit board within envelope, the circuit board having at least one electronic device mounted thereon;
a radio frequency transmitter mounted to the circuit board and generating radio frequency signals; and
an antenna coupled to the radio frequency transmitter within the envelope, signals broadcast from the antenna carrying sensor-generated information.

18. The sensor of claim 17 wherein the at least one electronic device is comprised of an accelerometer and wherein the sensor-generated information includes information from the accelerometer.

19. The sensor of claim 17 wherein the at least one electronic device is comprised of a temperature sensor and wherein the sensor-generated information includes information from the temperature sensor.

20. The sensor of claim 17 wherein the electronic device is comprised of a capacitance converter configured to measure capacitance between substantially rectangular conductive panels and configured to output a signal representative of said capacitance and wherein the sensor-generated information includes information from the capacitance converter.

21. The sensor of claim 17, wherein the wherein the electronic device is comprised of a resistance converter configured to measure an electrical resistance between the first and second substantially rectangular conductive panels and wherein the sensor-generated information includes information from the resistance converter.

22. The sensor of claim 17, wherein the electronic device is comprised of a microphone and wherein the sensor-generated information includes information from the microphone.

* * * * *